United States Patent [19]

Jering et al.

[11] Patent Number: 4,458,015

[45] Date of Patent: Jul. 3, 1984

[54] REAGENT FOR THE OPTICAL DETERMINATION OF THE BLOOD COAGULATION

[75] Inventors: Helmut Jering; Udo Becker, both of Munich; Peter Roeschlau, Seeshaupt, all of Fed. Rep. of Germany

[73] Assignee: Boehringer Mannheim GmbH, Mannheim, Fed. Rep. of Germany

[21] Appl. No.: 360,099

[22] Filed: Mar. 19, 1982

[30] Foreign Application Priority Data

Apr. 2, 1981 [DE] Fed. Rep. of Germany ....... 3113350

[51] Int. Cl.$^3$ .......................... C12Q 1/56; C12N 9/99
[52] U.S. Cl. ..................................... 435/13; 435/184; 435/810
[58] Field of Search ..................... 435/13, 23, 24, 810, 435/184

[56] References Cited

U.S. PATENT DOCUMENTS

| | | | |
|---|---|---|---|
| 3,183,159 | 5/1965 | Singher et al. | 435/13 |
| 3,228,841 | 1/1966 | Cohen et al. | 435/13 |
| 4,070,245 | 1/1978 | Svendsen | 435/13 |
| 4,169,015 | 9/1979 | Ekenstam et al. | 435/13 |

FOREIGN PATENT DOCUMENTS 14039  1/1979  European Pat. Off. .............. 435/13

OTHER PUBLICATIONS

Yamada et al., Chemical Abstracts, 91:189205p, 290 (1979).
Shum et al., Chemical Abstracts, 77:45185v, 210–211 (1972).
Bayer et al., Chemical Abstracts, 83:158537d, (1975).
Liu et al., Chemical Abstracts, 83:129418k, 324 (1975).

*Primary Examiner*—Esther M. Kepplinger
*Attorney, Agent, or Firm*—Felfe & Lynch

[57] ABSTRACT

The present invention provides a reagent for the optical determination of blood coagulation behavior (Quick test), comprising thromboplastin, a synthetic thrombin substrate and a buffer, characterized by a content of non-proteolytically active thromboplastin.

8 Claims, 1 Drawing Figure

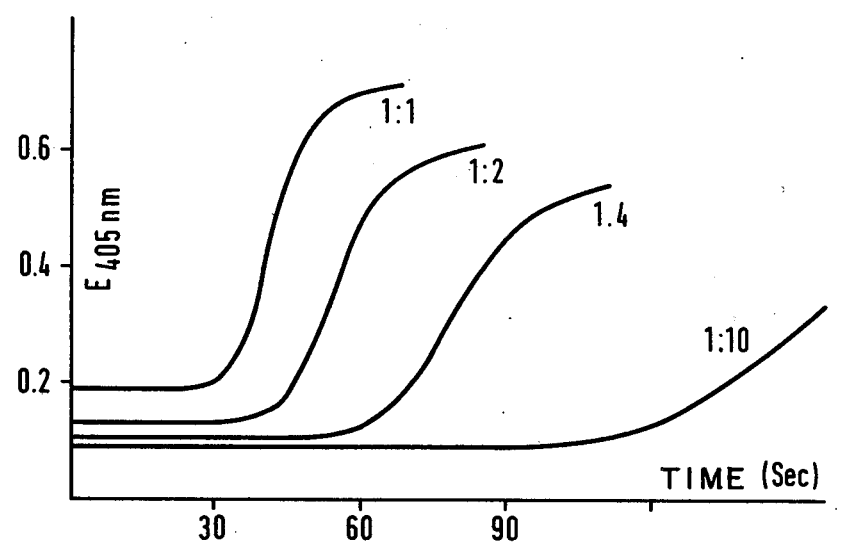

REAGENT FOR THE OPTICAL DETERMINATION OF THE BLOOD COAGULATION

This invention relates to a reagent for the optical determination of the blood coagulation behavior of the exogenic coagulation system referred to as the Quick test.

Coagulation-physiological investigations take place on a wide scale in hospitals, physicians' consulting rooms and laboratories inter alia for pre-operative investigations, for the recognition of a risk of haemorrhage or thrombosis, for monitoring an anti-coagulation therapy in the case of thrombosis-endangered patients and in the case of the continuing monitoring of numerous diseases, for example severe infections, liver function damage and malign diseases.

The coagulation tests most frequently carried out are global tests in which the function of several components participating in the coagulation process are determined simultaneously. The most important global test is the so-called prothrombin time test (Quick test, see A. J. Quick, Am. J. Physiol., 118, 260/1937) and the so-called activated partial thromboplastin time test (PTT). In the following, the "Quick test" is to be understood the determination of the blood coagulation behaviour of the exogenic coagulation system. This system is initiated by the liberation of thromboplastin from damaged tissue. The Quick test gives information regarding the functional state of the components regarded as belonging to the so-called exogenic coagulation system, whereas the PTT test permits a recognition of the functional state of the components participating in the endogenic coagulation system which is initiated by contact activation of Factor XII. In the case of a pathological result of the test, the defect can initially not be associated with a definite component. This must take place by a subsequent determination of individual coagulation factors, for which appropriate test systems are also known.

In the case of carrying out the coagulation-physiological test, the usual measured variable is most frequently the coagulation time, the time thereby being recorded which, after the addition of a reagent to the fluid being investigated, passes until the formation of a coagulum. Independently of the nature of the coagulation factors to be determined, the known tests are so arranged that finally the transformation of fibrinogen into fibrin is initiated by the enzyme thrombin. Therefore, the conversion of fibrinogen (soluble) into fibrin (insoluble) serves as an indicator reaction, apart from when fibrinogen itself is to be determined.

Numerous methods are known for the measurement of the commencement of coagulation. Most frequently, a platinum loop is periodically introduced in the coagulation batch and, upon formation of a coagulum, this loop withdraws a fibrin filament from the solution. This point of time is then recorded as the coagulation end point. The recordal procedure can take place manually by means of a stopwatch or electrically by initiation of contact when the platinum loop is made as an electrode. An automation in the sense of conventional clinical-chemical analysis is not possible with this system since a continuous throughput of samples is not possible, the coagulum cannot be washed away automatically and the loops cannot be sufficiently cleaned between analyses.

Another possibility for recording coagulation times is the turbidity which occurs upon coagulum formation and which is brought about by the formation of insoluble fibrin. Optically recording coagulometers are known which operate according to this principle. In practice, however, this principle is limited since many plasmas display a high inherent turbidity, the reagents used are, in some cases, themselves turbid and in pathological investigational material the coagulation can take place so slowly that a clear signal is not obtained.

The simplest possibility of avoiding turbidity problems would be to operate at high dilution. However, in the case of the known process, this is not always possible since, simultaneously with the dilution, the reaction time of the coagulation test is considerably lengthened and the possible advantage of automation is again lost due to the extended reaction times. Beyond a certain dilution, the fibrinogen contained in the sample no longer suffices for the indicator reaction, which consists in the conversion of fibrinogen into fibrin. Plasma diluted 1:10 has, for example, in comparison with undiluted plasma in the Quick test, a coagulation time prolonged about 3 to 5 fold. The extent of the prolongation of coagulation times by dilution has been quantitatively described inter alia by Biggs (Proc. Royal Soc., 173, 421–441/1969) and by Girolami (Blut, 28, 351–360/1974).

Especially greatly prolonged reaction times are obtained when, in addition to the sample dilution, the reagents are also diluted (see Biggs loc. cit.). However, a reagent dilution is also to be regarded as being a prerequisite for an optical measurement of coagulation processes which are free from turbidity problems. Thus, the reagents used in coagulation diagnosis possess an inherent turbidity directly connected with their function. The tissue thromboplastins used for carrying out the Quick test are milky turbid suspensions of mammalian tissues, for example of rabbit brain.

Methods and reagents have already been described which can be used for carrying out global coagulation tests in dilute media. They depend upon the use of synthetic chromogenic peptide substrates for carrying out the indicator reaction since, as mentioned, in the case of predilution, the fibrinogen content of the sample is no longer sufficient, the synthetic chromogenic substrates thereby taking the place of the natural substrate fibrinogen. The optical signal results from a splitting of the substrate by thrombin, which liberates an optically determinable fragment (see Paulsen et al., Clinica Chimica Acta, 92, 465–468/1979; Yamada et al., Thrombosis Research, 15, 351–358/1979; and European Patent Specification No.0014039).

A disadvantage of the process using a synthetic substrate and of thromboplastin for the optical Quick test is that it is not possible to provide a pre-mixed single component reagent which contains all the substances necessary for carrying out the test. Thus, thromboplastin displays a proteolytic action which results in a splitting of the substrate and thus falsifies the substrate splitting by the thrombin formed. Furthermore, such a reagent would also not be storage-stable.

It is an object of the present invention to solve this problem and to provide a reagent which contains all the substances needed for carrying out the test, is storage-stable and provides the correct results.

Thus, according to the present invention, there is provided a reagent for the optical determination of blood coagulation behaviour (Quick test), comprising thromboplastin, a synthetic thrombin substrate and a buffer, characterised by a content of non-proteolytically-active thromboplastin.

A thromboplastin which can be used for the reagent according to the present invention is obtainable by preparing an acetone-dry powder from an appropriate tissue, preferably brain, incubating a neutral aqueous solution of the acetone-dry powder at 25° to 40° C., isolating the insoluble fraction thereby formed, suspending it in a dilute salt solution, treating the suspension with a surface-active agent in the presence of formate and finally drying the solution freed from insoluble components.

The preparation of an acetone-dry powder from the tissue material can be carried out by any method known for the preparation of acetone-dry powder. One such process is, for example, described by R. Biggs, "Human Blood Coagulation, Haemostasis and Thrombosis", pub. Blackwell Scientific Publications, Oxford, 1976, page 663.

The acetone-dry powder is suspended in a neutral aqueous solution and incubated, while stirring, at the given temperature, a temperature of from 35° to 40° C. being preferred. Under these conditions, the incubation takes about half an hour. The pH value can thereby be from 6.0 to 8.0 and is preferably from 6.7 to 7.3. It is preferably kept constant by means of an appropriate buffer. The insoluble fraction can be separated off by centrifuging, for example at 2500 g. The precipitate obtained by centrifuging is again suspended in a dilute salt solution and preferably treated with a surface-active agent of the cholic acid group in the presence of formate. For the salt solution, it is preferred to use sodium chloride. Appropriate concentrations for the salt solution are from 0.2 to 2% and preferably from 0.5 to 1%. The concentration of the surface-active agent is preferably from 0.01 to 0.2%, especially when the preferred cholates are used. However, other surface-active agents can also be employed.

As formate, the alkali metal and alkaline earth metal formates are preferred, calcium formate being especially preferred. The concentration of the formate is preferably from 0.005 to 0.05 mol/liter. The treatment is preferably also carried out in a temperature range of from 25° to 40° C., the period of time corresponding to that used for the incubation of the dry powder. Finally, it is centrifuged, for example at 2500 xg, and the suspension obtained of a no longer proteolytically active thromboplastin, possibly after the previous addition of the other components of the reagent according to the present invention, is freeze-dried. The reagent can, however, also be mixed together from the solid dry substances in the desired amount ratio.

As synthetic thrombin substrate, use can, in principle, be made of any of the known synthetic thrombin substrates. Numerous thrombin substrates of this kind are commercially available. The substrate Tos-Gly-Pro-Arg-pNA, is preferred, as well as H-D-Phe-Pip-Arg-pNA, which is available under the designation S-2238. Upon enzymatic splitting, these substrates give coloured fission products which can easily be quantitatively determined optically.

The reagent according to the present invention contains thromboplastin in a concentration of from 3 to 20 vol. % and preferably of 6 to 10 vol. %, with an activity as described hereinafter in Example 1, synthetic thrombin substrate in an amount of from $2 \times 10^{-5}$ to $20 \times 10^{-5}$ mol/liter, as well as buffer (pH 7.2 to 8.5), the buffer concentration preferably being from 0.05 to 0.25 mol/liter. In principle, use can be made of any buffer which is effective in the given pH range, tris buffer being especially preferred. The best results have been obtained with 0.1 mol/liter buffer (pH 8.1). The especially preferred substrate concentration is $5 \times 10^{-5}$ mol/liter.

Furthermore, the reagent according to the present invention preferably also contains calcium salts in a concentration of from 2 to 10 mmol/liter, referred, as are the above, to the final reagent solution. The calcium salt can be any readily soluble calcium salt, for example a halide, acetate or the like, calcium chloride being preferred.

In addition, the reagent preferably also contains 0.5 to 3 wt. % of urea and especially preferably 1.4 to 1.6% thereof.

A reagent according to the present invention of the above composition is admittedly, in the form of a solution ready for use, a dilute system but the period of reaction in comparison with the known tests in an undiluted system is, however, not substantially prolonged. In the case of normal plasma, the determination takes about 30 seconds and in the case of plasma from subjects who are receiving thrombosis prophylaxis by means of oral anti-coagulants, takes about 60 to 120 seconds. In the case of the known undiluted Quick test with the above-described disadvantages, the corresponding times for normal plasma are about 15 seconds and in the case of the mentioned pathological plasma 30 to 60 seconds. In comparison thereto, the known tests comparable with regard to the dilution with the reagent according to the present invention, require an about five-fold reaction time.

The reagent according to the present invention is preferably employed in such a manner that the time up to reaching a particular absorption at a given wavelength is measured. However, a kinetic evaluation is also possible, in which case it is preferable to prepare a calibration curve for the evaluation. The period of determination, which is substantially shortened in comparison with the known optical Quick tests, is attributable to a synergistic effect of the ionic strength and pH values lying outside of the physiological range and to the substrate concentration lying below the $K_M$.

The following Examples are given for the purpose of illustrating the present invention:

EXAMPLE 1

(A) Preparation of Non-Proteolytic Thromboplastin

A dry powder is obtained from freshly obtained rabbit brain by acetone treatment by the process described by R. Biggs ("Human Blood Coagulation, Haemostasis and Thrombosis", pub Blackwell Scientific Publications, Oxford, 1976, page 663) and dried to constant weight.

2.5 g. of the above powder are suspended in 50 ml. 0.1 mol/liter sodium acetate buffer (pH 7) and stirred for 30 minutes at 37° C. Thereafter, it is centrifuged for 15 minutes at 2500 g and the precipitate again stirred for 30 minutes at 37° C. in 50 ml. of 0.7% sodium chloride solution which contains 0.05% sodium desoxycholate and 0.0125 mol/liter calcium formate. It is then again centrifuged for 15 minutes at 2500 g.

The supernatant obtained contains thromboplastin without proteolytic activity.

The activity of the thromboplastin suspension is determined by means of the Quick test, carried out according to German Industrial Standard DIN 58910. A normal reference plasma prepared according to this Industrial Standard has a coagulation time of 12±2 seconds.

(B) Preparation of a Reagent Mixture for Carrying Out an Optical Quick Test

Solution 1:
0.1 mol tris/HCl, pH 8.1, containing 2% glycine

Solution 2:
Aqueous solution of Tos-Gly-Pro-Arg-pNA acetate, 497 mg./dl.

Solution 3:
Thromboplastin suspension prepared according to (A) above.

10 Parts by volume of Solution 1 are mixed with 4 parts by volume of Solution 3 and 1 part by volume of Solution 2 and 3 ml. aliquots thereof are lyophilised.

EXAMPLE 2

Carrying Out an Optical Quick Test

For carrying out the test, 3 ml. of the lyophilisate obtained according to Example 1 (B) are dissolved in 30 ml. tris/HCl buffer (pH 8.1), which additionally contains 1.5% urea and 6 mmol/liter calcium chloride. The reaction mixture is adjusted to 37° C. Photometer used: measurement temperature 37° C., wavelength 405 nm.

50 µl. amounts of sample are taken (citrate plasma or dilutions of citrate plasma in physiological sodium chloride solution) and the reaction started with 750 µl. of reaction mixture. At the same time, a recorder is started (10 cm./min.).

The curves shown in FIG. 1 of the accompanying drawing are obtained when there is successively used undiluted plasma and 1:2, 1:4 and 1:10 prediluted plasma.

EXAMPLE 3

From the course of the curves obtained according to Example 2 there is taken the time up to the achievement of an extinction which is 30 mE higher than the initial extinction. These times are plotted against the reciprocal plasma dilutions. A straight line is obtained. The pre-selected extinction of 30 mE can be varied within wide ranges, for example from 10 to 150 mE, a straight line always being obtained.

EXAMPLE 4

Corresponding to Example 2, 60 plasma samples are taken from patients who are receiving oral anticoagulant therapy and these tested undiluted, the time being recorded up to the achievement of an extinction lying 30 mE higher than the initial value. The same plasma were tested by means of a conventional Quick test with the use of a coagulometer according to Schnitker and Gross and the coagulation times recorded. The data obtained in both systems are subjected to a linear regression analysis, a correlation coefficient of r=0.96 being obtained.

EXAMPLE 5

Corresponding to Example 1 (B), reagent mixtures are prepared with the use of a non-proteolytic thromboplastin prepared according to Example 1 (A), as well as of a commercially available thromboplastin (thromboplastin a, Boehringer Mannheim). The reagent mixtures are diluted with tris/HCl buffer (pH 8.1) according to Example 2 to give the final reaction mixture and this is stored at ambient temperature (about 20° C.). The inherent extinction of the reaction mixtures was measured at definite intervals of time at 405 nm. The results obtained are given in the following Table. In the case of the commercially available thromboplastin, a rapid increase of extinction is found, which is due to a splitting of the added chromogenic peptide substrate.

TABLE

| | extinction at 405 nm | |
|---|---|---|
| incubation time (days) | commercially available thromboplastin | thromboplastin prepared according to Example 1 |
| 0 | 0.008 | 0.000 |
| 0.3 | 0.012 | 0.003 |
| 1.0 | 0.028 | 0.010 |
| 2.0 | 0.049 | 0.015 |
| 5.0 | 0.108 | 0.030 |
| 7.0 | 0.154 | 0.035 |

It will be understood that the specification and examples are illustrative but not limitative of the present invention and that other embodiments within the spirit and scope of the invention will suggest themselves to those skilled in the art.

What is claimed is:

1. Reagent for the optical determination of blood coagulation behavior (Quick test), comprising thromboplastin, a synthetic thrombin substrate and a buffer in the range of pH 7.2 to 8.5, said thromboplastin being non-proteolytically-active so as to develop only about 22.7 to 35.7% of the extinction at 405 nm as compared with normal thromboplastin when each is incubated for a period of one to seven days at about 20° C. with tris-HCl buffer of pH 8.1 in the presence of chromogeneous substrate.

2. Reagent as claimed in claim 1, wherein the non-proteolytically active thromboplastin is obtained by preparing an acetone dry powder from brain tissue, incubating a neutral aqueous solution of the acetone dry powder at 25° to 40° C., obtaining the insoluble fraction, treating a suspension of this fraction in a dilute salt solution with a surface-active agent in the presence of formate and drying the separate soluble fraction.

3. Reagent as claimed in claim 1, comprising the non-proteolytic thromboplastin in a concentration of 3 to 20 vol. %, $2 \times 10^{-5}$ to $20 \times 10^{-5}$ mol/liter of synthetic thrombin substrate, 0.05 to 0.25 mol/liter of buffer (pH 7.2 to 8.5) and 2 to 10 mmol/liter of soluble calcium salt.

4. Reagent as claimed in claim 3, additionally containing 0.5 to 3% urea.

5. Reagent as claimed in claim 3, wherein the buffer is a tris buffer.

6. Method for the optical determination of blood coagulation behavior (Quick test) which method comprises contacting a reagent as claimed in claim 1 with a blood sample and measuring the optical characteristics of the resulting mixture as a measure of the blood coagulation behavior of said sample.

7. Method as claimed in claim 6, wherein the time up to reaching a particular absorption value at a given wave length is measured.

8. Method as claimed in claim 6, wherein a kinetic evaluation is carried out by means of a calibration curve.

* * * * *